US012779190B2

(12) United States Patent
Lim et al.

(10) Patent No.: US 12,779,190 B2
(45) Date of Patent: Nov. 3, 2026

(54) TRANSDERMAL DRUG DELIVERY PATCH AND MANUFACTURING METHOD THEREOF

(71) Applicant: POSTECH ACADEMY-INDUSTRY FOUNDATION, Pohang-si (KR)

(72) Inventors: Geunbae Lim, Pohang-si (KR); Jungho Lee, Siheung-si (KR); Byoungsun Choi, Daegu (KR); Hyeonsu Woo, Pohang-si (KR)

(73) Assignee: POSTECH ACADEMY-INDUSTRY FOUNDATION, Pohang-si (KR)

( * ) Notice: Subject to any disclaimer, the term of this patent is extended or adjusted under 35 U.S.C. 154(b) by 0 days.

(21) Appl. No.: 18/739,540

(22) Filed: Jun. 11, 2024

(65) Prior Publication Data

US 2024/0325702 A1 Oct. 3, 2024

Related U.S. Application Data

(62) Division of application No. 17/055,653, filed as application No. PCT/KR2018/005738 on May 18, 2018, now Pat. No. 12,036,378.

(51) Int. Cl.

| | |
|---|---|
| ***A61M 37/00*** | (2006.01) |
| ***A61K 9/00*** | (2006.01) |
| ***A61K 9/70*** | (2006.01) |

(52) U.S. Cl.

CPC ....... *A61M 37/0015* (2013.01); *A61K 9/0021* (2013.01); *A61K 9/7046* (2013.01); *A61M 2037/0023* (2013.01); *A61M 2037/0053* (2013.01)

(58) Field of Classification Search

CPC ................ A61K 9/7046; A61K 9/0021; A61K 41/0047; A61K 9/7092; A61K 9/7084; A61K 9/7038; A61K 9/7023; A61M 37/0015; B29C 33/3885; B29C 33/3878; B29C 33/3857; B29C 33/3842

See application file for complete search history.

(56) References Cited

U.S. PATENT DOCUMENTS

| | | | | |
|---|---|---|---|---|
| 2013/0338632 A1* | 12/2013 | Kaplan | ................. | A61L 31/125 604/173 |
| 2018/0250503 A1* | 9/2018 | Enomoto | .............. | A61M 37/00 |

* cited by examiner

*Primary Examiner* — Stella K Yi

(74) *Attorney, Agent, or Firm* — LEX IP MEISTER, PLLC

(57) ABSTRACT

A transdermal drug delivery patch according to an exemplary embodiment of the present invention includes: a flexible base layer; and a plurality of microneedle disposed at one surface of the base layer. Each of the plurality of microneedles includes a biodegradable polymer and a drug and has an empty space inside. Each of the plurality of microneedles is formed as a star-shaped pyramid including a plurality of protrusions extending in a radial direction, and a part between two protrusions adjacent along the circumferential direction among the plurality of protrusions is concave.

6 Claims, 26 Drawing Sheets

100

TRANSDERMAL DRUG DELIVERY PATCH AND MANUFACTURING METHOD THEREOF

TECHNICAL FIELD

The present invention relates to a transdermal drug delivery patch. More particularly, the present invention relates to a transdermal drug delivery patch and a manufacturing method thereof for improving mechanical strength of a microneedle with an empty space inside.

BACKGROUND ART

A transdermal drug delivery patch (hereinafter, referred to as 'a patch' for convenience) includes a micro-needle made of a biodegradable polymer loaded with a drug.

The microneedle penetrates the stratum corneum of skin, penetrates into the epidermis or dermis of the skin, and stay in the skin for several minutes to several hours to allow a drug to decompose by body fluids and to be absorbed into the body. Unlike a conventional syringe, these patches cause little bleeding and pain in the drug delivery process.

The microneedle is loaded with the drug at the pointed end, and the central portion may be formed with a hollow shape. The patch equipped with such a microneedle may be quickly separated from the skin after leaving only the drug on the skin, and the time required to maintain the attached state to the skin can be shortened. However, as the size of the hollow space increases, the mechanical strength of the microneedle weakens, thereby it may be impossible to penetrate the skin.

In addition, as the surface area of the microneedle is wider than the volume, the area in contact with the body fluid of the skin is enlarged, and the biodegradable polymer is rapidly dissolved, thereby increasing the absorption efficiency of the drug. However, for convenience of manufacturing, the conventional patch mainly has the microneedles that have a simple shape such as a cone or a quadrangular pyramid and have a small surface area compared to the volume, so there is a limitation in enhancing the absorption efficiency of the drug.

DISCLOSURE

Technical Problem

The present invention is to provide a transdermal drug delivery patch and a manufacturing method thereof that may improve penetration efficiency into the skin and absorption efficiency of the drug by increasing the mechanical strength of the hollow microneedle and simultaneously expanding the surface area compared to the volume.

Technical Solution

A transdermal drug delivery patch according to an exemplary embodiment of the present invention includes a flexible base layer, and a plurality of microneedles disposed at one surface of the base layer. Each of the plurality of microneedles includes a biodegradable polymer and a drug, and has an empty space inside. Each of the plurality of microneedles is formed as a star-shaped pyramid including a plurality of protrusions extending in a radial direction, and a part between two protrusions adjacent along the circumferential direction among the plurality of protrusions is concave.

An opening of each empty space of the plurality of the microneedles may be disposed in the base layer.

In each of the plurality of microneedles, all protruded lengths of each of a plurality of protrusions according to the radial direction may be the same, and all distances between two protrusions adjacent along the circumferential direction among a plurality of protrusions may be the same. The plurality of protrusions may be 3 or more and 20 or less.

In each of a plurality of microneedles, the drug may be concentrated at the pointed end portion of the microneedle. On the other hand, in each of a plurality of microneedles, the drug may be uniformly distributed on the entire microneedle.

A manufacturing method of a transdermal drug delivery patch according to an exemplary embodiment of the present invention includes: (1) manufacturing a master mold including a transparent plate and a plurality of protruded parts disposed at one surface of the transparent plate and made as a star-shaped pyramid including a plurality of protrusions extending in a radial direction; (2) manufacturing a master mold including a plurality of recess portions having a shape corresponding to a plurality of protruded parts by using the master mold; and (3) manufacturing a transdermal drug delivery patch including a base layer and a plurality of microneedles having a shape corresponding to a plurality of recess portions while having an empty space inside by using the mold, and a drug and a biodegradable polymer solution.

The manufacturing of the master mold may include: forming a photo-curable polymer layer on a transparent plate; disposing a grayscale mask between a light source and the transparent plate; and irradiating light to the photo-curable polymer layer through the grayscale mask for a process of curing a part of the photo-curable polymer layer.

The grayscale mask may include a star-shaped light transmission part including a plurality of protrusions extending in a radial direction and a light blocking part other than the light transmission part, and a light transmission rate of the light transmission part may become smaller further away from the center of the light transmission part.

The light transmission part may be composed of a plurality of dots, and the plurality of dots may have a smaller size further away from the center of the light transmission part. On the other hand, the light transmission part may be composed of a plurality of dots of the same size, and the further away from the center of the light transmission part, the greater the distance between the plurality of dots.

The manufacturing of the mold may include: coating a polymer solution on the master mold to form a polymer layer; and applying heat to the polymer layer to be cured. Before curing the polymer layer, a negative pressure may be applied to the polymer layer to remove microbubbles included in the polymer layer.

The manufacturing of the transdermal drug delivery patch may include: filling a drug at each pointed end portion of a plurality of recess portions included in the mold; coating a biodegradable polymer solution at the mold surface between each wall surface of a plurality of recess portions and the plurality of recess portions; manufacturing the base layer and a plurality of microneedles by drying the drug and the biodegradable polymer solution; and separating the base layer and the plurality of microneedles from the mold.

Before drying the drug and the biodegradable polymer solution, a vacuum filter and a vacuum chamber may be disposed at the rear of the mold, a vacuum pump connected to the vacuum chamber may be operated, and a negative pressure in a single direction may be applied to the drug and the biodegradable polymer solution through the mold and a vacuum filter to remove microbubbles included in the drug and the biodegradable polymer solution.

On the other hand, the manufacturing of the transdermal drug delivery patch may include: coating a material solution in which a biodegradable polymer solution and a drug are mixed to each wall surface of the plurality of recess portions included in the mold; coating a biodegradable polymer solution to the mold surface of a plurality of recess portions; drying the material solution and the biodegradable polymer solution to manufacture the base layer and a plurality of microneedles; and separating the base layer and the plurality of microneedles from the mold.

Before drying the material solution and the biodegradable polymer solution, a vacuum filter and a vacuum chamber may be disposed at the rear of the mold, a vacuum pump connected to the vacuum chamber is operated, and a negative pressure of a single direction may be applied to the material solution and the biodegradable polymer solution through the mold and the vacuum filter to remove microbubbles included in the material solution and the biodegradable polymer solution.

Advantageous Effects

According to the present invention, the microneedles composed as the star-shaped pyramid have an enlarged surface area by the protruded shape of the protrusions and the concave shape between the protrusions and has high mechanical strength. Therefore, the skin penetration efficiency of the microneedles and the absorption efficiency of the drug may be improved, and the drug may be absorbed into the body in a shorter time.

MODE FOR INVENTION

The present invention will be described more fully hereinafter with reference to the accompanying drawings, in which exemplary embodiments of the invention are shown. As those skilled in the art would realize, the described embodiments may be modified in various different ways, all without departing from the scope of the present invention.

Figure 1:
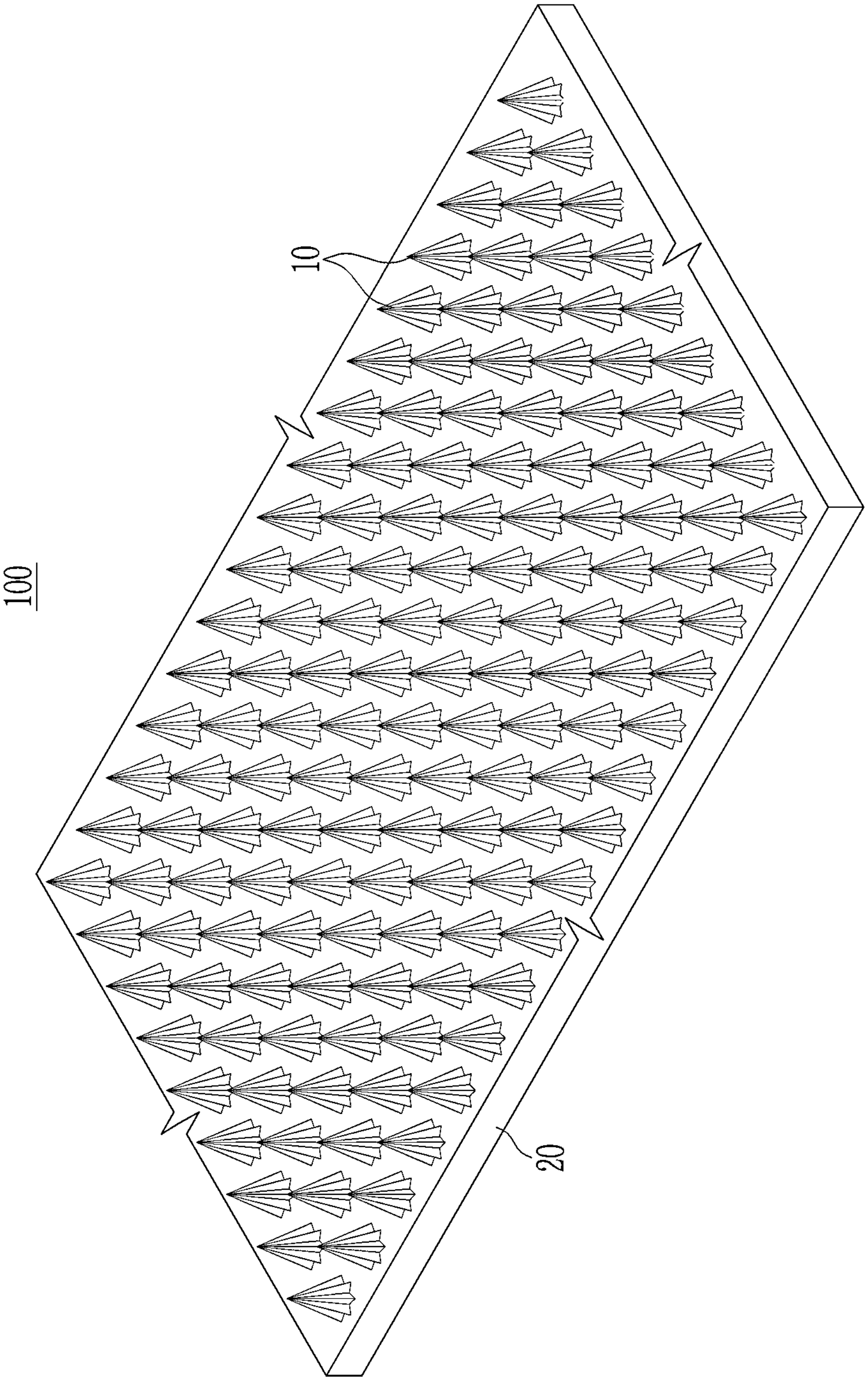
FIG. 1 is a perspective view of a transdermal drug delivery patch according to an exemplary embodiment of the present invention.
Figure 2:
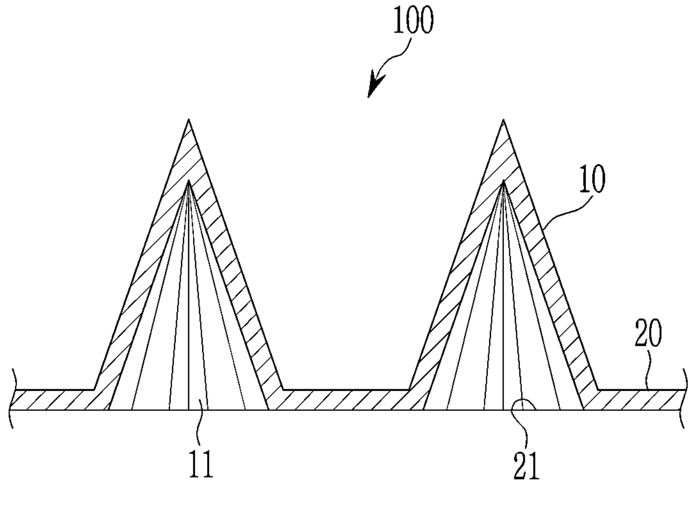
FIG. 2 is a partial enlarged cross-sectional view of a transdermal drug delivery patch shown in FIG. 1.
Figure 3:
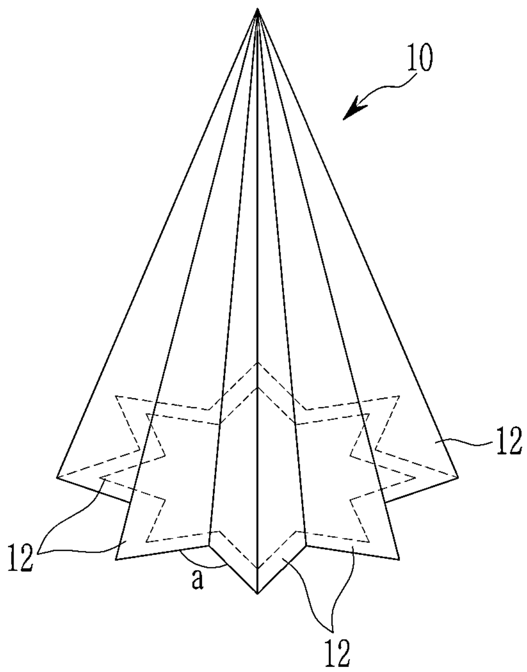
FIG. 3 is an enlarged perspective view of one microneedle of a transdermal drug delivery patch shown in FIG. 1.
Figure 4:
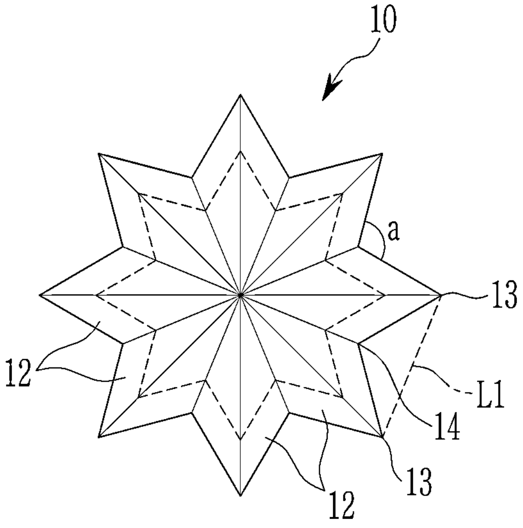
FIG. 4 is a top plan view of a microneedle shown in FIG. 3.

FIG. 1 is a perspective view of a transdermal drug delivery patch according to an exemplary embodiment of the present invention, and FIG. 2 is a partial enlarged cross-sectional view of a transdermal drug delivery patch shown in FIG. 1. FIG. 3 is an enlarged perspective view of one microneedle of a transdermal drug delivery patch shown in FIG. 1, and FIG. 4 is a top plan view of a microneedle shown in FIG. 3.

Referring to FIG. 1 to FIG. 4, a patch 100 of the present exemplary embodiment is composed of a plurality of microneedles 10 having an empty space 11 therein and a base layer 20 that integrally connects the plurality of microneedles 10 by contacting the plurality of microneedles 10. A plurality of microneedles 10 are aligned on one surface of the base layer 20 at a distance from each other.

A plurality of openings 21 may be disposed in the base layer 20, and each empty space 11 of a plurality of microneedles 10 may communicate with the openings 21. That is, the empty space 11 of the microneedle 10 may be an open space toward the rear. The base layer 20 is a flexible supporter that supports a plurality of microneedles 10, and may be composed of a biodegradable polymer film having a predetermined thickness that is easily bent to be suitable to the curvature of the skin.

A plurality of microneedles 10 may have the same size and the same shape and may be aligned side by side on the base layer 20. The microneedle 10 is made of a biodegradable polymer dispersed with the drug in a powder or liquid form, and penetrates a stratum corneum of the skin and penetrates into an epidermis or dermis of the skin. The drug may be concentrated on the pointed tip of the microneedle 10 or uniformly distributed throughout microneedle 10.

The biodegradable polymer constituting the patch 100 may include at least one of hyaluronic acid, carboxymethyl cellulose, and polyvinyl alcohol, but is not limited to this example. The microneedle 10 is decomposed by a body fluid while staying in the epidermis or dermis of the skin for several minutes to several hours to absorb the drug into the body.

In the patch 100 of the present exemplary embodiment, the microneedle 10 is made as a star-shaped pyramid including a plurality of protrusions 12 extending in the radial direction. In the entire specification, 'the radial direction' refers to the direction extending from the center of the microneedle 10 in all directions when viewing the microneedle 10 from the top (i.e., on the plane of the microneedle 10).

In FIG. 3 and FIG. 4, the microneedle 10 made as an octagonal star-shaped pyramid is shown as an example.

A plurality of protrusions 12 extend parallel to the radial direction from the center of the microneedle 10, and the size of the protrusions 12 gradually decreases as the distance from the base layer 20 increases. Further, among a plurality of protrusions 12, a concave shape is formed between two adjacent protrusions 12 along the circumferential direction. In the entire specification, 'the circumferential direction' means the direction to surround the microneedle 10 once.

The fact that a plurality of protrusions 12 extend in the radial direction and the two protrusions 12 adjacent along the circumferential direction form the concave shape is an important shape characteristic that distinguishes it from a microneedle having a polygonal pyramid shape such as a quadrangular pyramid.

Figure 5:
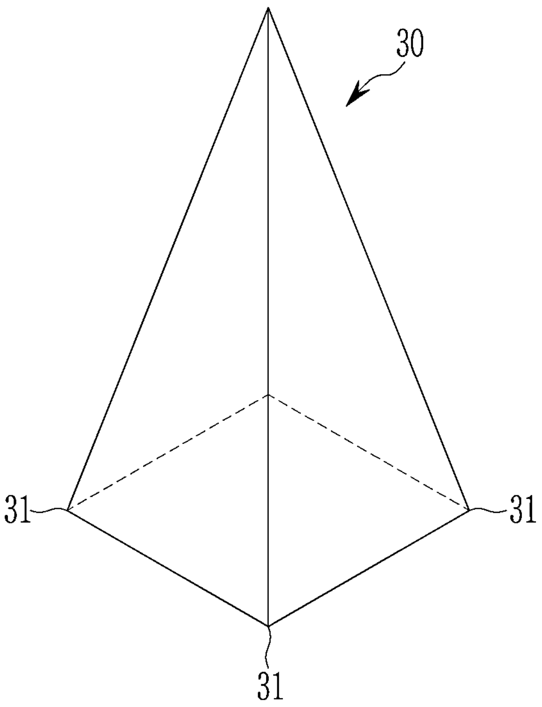
FIG. 5 is a perspective view showing a microneedle made with a quadrangular pyramid shape according to a comparative example.

FIG. 5 is a perspective view showing a microneedle made with a quadrangular pyramid shape according to a comparative example. Referring to FIG. 5, the microneedle 30 with the quadrangular pyramid shape has four corners 31 when viewed from above, and a straight line is formed between two corners 31 adjacent to each other among the four corners 31.

Again referring to FIG. 3 and FIG. 4, in the patch 100 according to the present exemplary embodiment, when assuming an imaginary line L1 that connects two protrusions 12 adjacent along the circumferential direction to a shortest distance among a plurality of protrusions 12 included in the microneedle 10, the space between the two protrusions 12 is disposed more inward toward the center of the microneedle 10 than this imaginary line L1.

Specifically, each of a plurality of protrusions 12 is composed of a pointed end 13 and a root portion 14 connected to the neighboring protrusions 12, and the root portion 14 is disposed more inward toward the center of the microneedle 10 than the imaginary line that connects two pointed ends 13 adjacent along the circumferential direction with the shortest distance.

Each protruded length of a plurality of protrusions 12 according to the radial direction may be the same, and a distance between two end portions 13 adjacent to each other according to the circumferential direction among the plurality of protrusions 12 may be the same. That is, the microneedle 10 may achieve rotational symmetry. The microneedles 10, which have a rotationally symmetrical shape, may uniformly contact the body fluid on the entire surface to increase the decomposition efficiency of the biodegradable polymer.

The microneedle 10 composed of the star-shaped pyramid has an enlarged surface area and has high mechanical strength by the protruded shape of the protrusions 12 and the concave shape between the protrusions 12. In other words, the microneedle 10 has an enlarged surface area and improved mechanical strength compared to a microneedle of a conical or quadrangular pyramid shape having an empty space of the same height and volume.

When the microneedle 10 is penetrated into the epidermis or dermis of the skin, the wider the surface area, the wider the contact with the body fluids, and the faster the absorption speed of the body fluid. Therefore, the biodegradable polymer that constitutes the microneedle 10 may quickly dissolve and release the drug quickly.

Meanwhile, the empty space 11 of the microneedle 10 has the effect of quickly separating the patch 100 from the skin and shortens the time required to keep the patch 100 attached to the skin, but it deteriorates the mechanical strength of the microneedle 10. The microneedle 10 of the present exemplary embodiment has improved mechanical strength due to the stable many-sidedness star shape of a plurality of protrusions 12 and may easily penetrate the skin and deliver the drug into the body.

The number of the protrusions 12 constituting the microneedle 10 in the patch 100 of the present exemplary embodiment is not limited to eight, and may be variously changed. Specifically, the number of the protrusions 12 constituting the microneedle 10 is 3 or more, and preferably may belong to the range of 3 to 20.

When the number of the protrusions 12 is 3 or more, the microneedle 10 may implement a star-shaped pyramid. When the number of the protrusions exceeds 20, the manufacturing process of the patch 100 is complicated, and the surface area enlargement effect is small compared to the cone.

Figure 6:
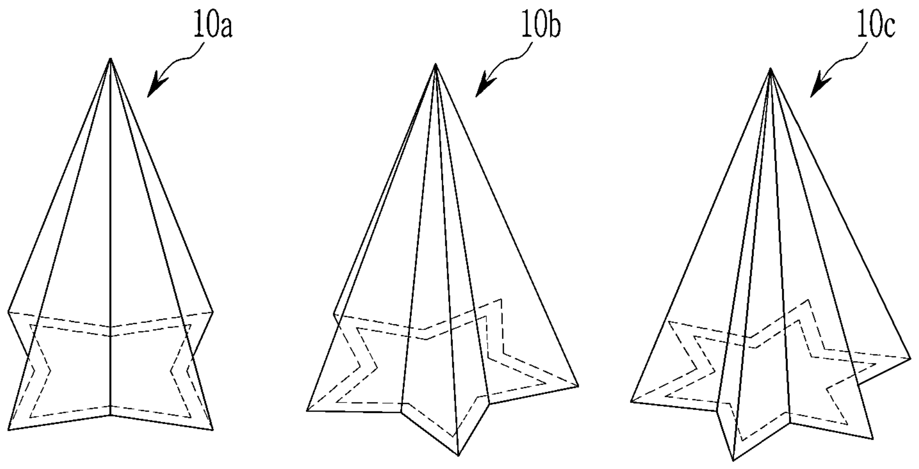
FIG. 6 is a perspective view showing microneedles according to exemplary variations that may be implemented.

FIG. 6 is a perspective view showing microneedles according to exemplary variations that may be implemented. In FIG. 6, the micro-needle 10*a* with the quadrangle star shape of a pyramid for each square, the micro-needle 10*b* with the pentagon star shape of a pyramid, and the microneedle 10*c* with the hexagonal shape of a pyramid are shown as examples.

Again referring to FIG. 1 to FIG. 4, the patch 100 of the present exemplary embodiment may increase the mechanical strength of the microneedle 10 while maintaining a high aspect ratio of the microneedle 10 and effectively enlarge the surface area. As a result, the skin penetration efficiency of the microneedle 10 and the absorption efficiency of the drug may be improved, and the drug may be absorbed into the body in a shorter time.

Figure 7:
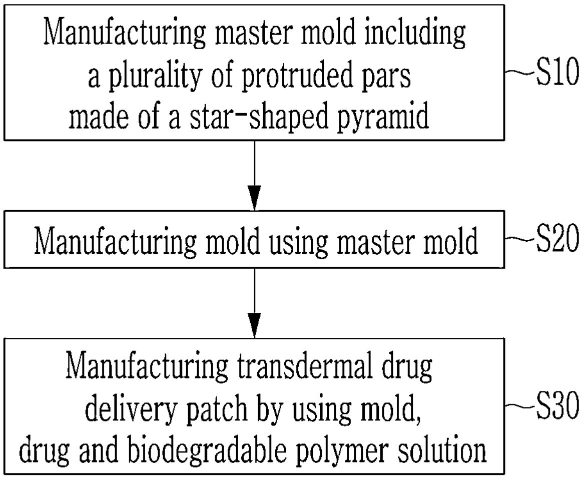
FIG. 7 is a process flowchart showing a manufacturing method of a patch according to an exemplary embodiment of the present invention.

Next, the manufacturing method of the patch according to the present exemplary embodiment is described. FIG. 7 is a process flowchart showing a manufacturing method of a patch according to an exemplary embodiment of the present invention.

Referring to FIG. 7, the manufacturing method of the patch includes a first step (S10) of manufacturing a master mold including a plurality of protruded parts made as a star-shaped pyramid, a second step (S20) of manufacturing a mold by using the master mold, and a third step (S30) of manufacturing a patch including a plurality of microneedles and a base layer by using the mold.

FIG. 8A to FIG. 8D are views showing a master mold manufacturing process of a first step shown in FIG. 7.

Figure 8A:
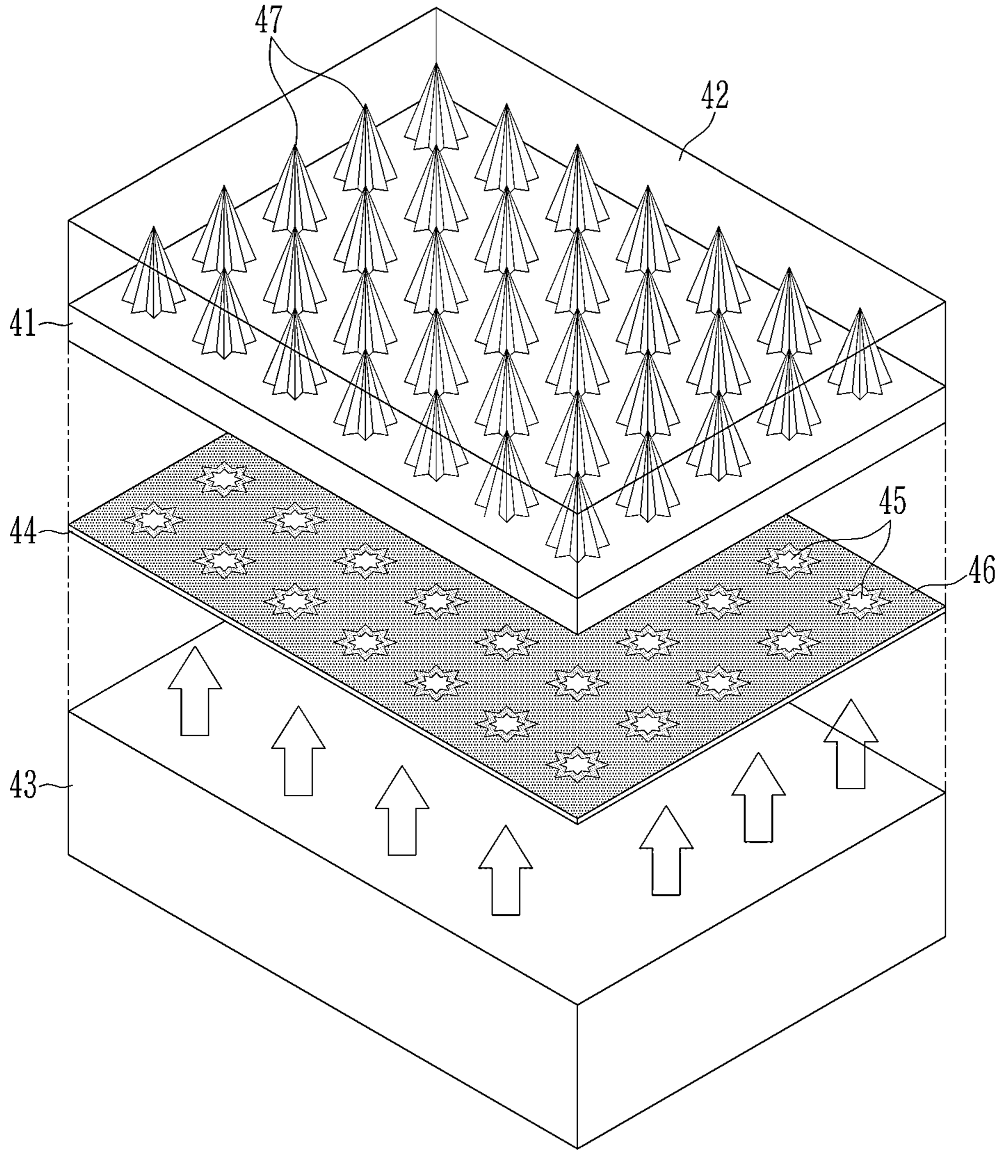
FIG. 8A to FIG. 8D are views showing a master mold manufacturing process of a first step shown in FIG. 7.
Figure 8B:
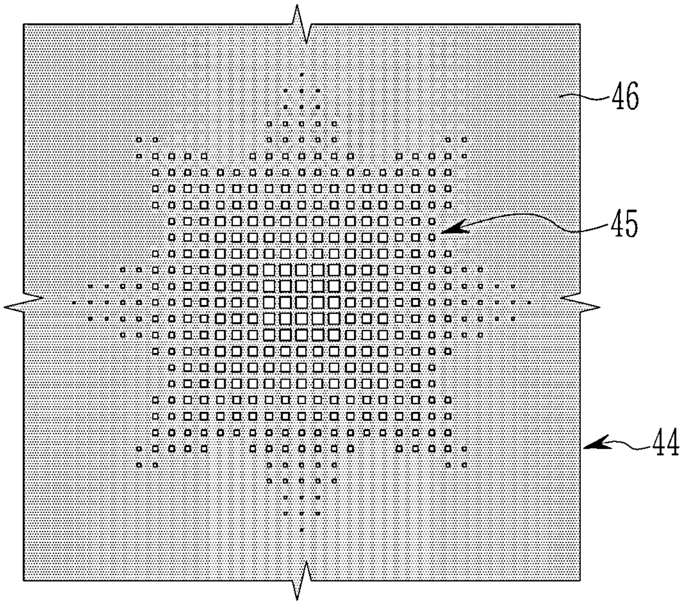
Figure 8C:
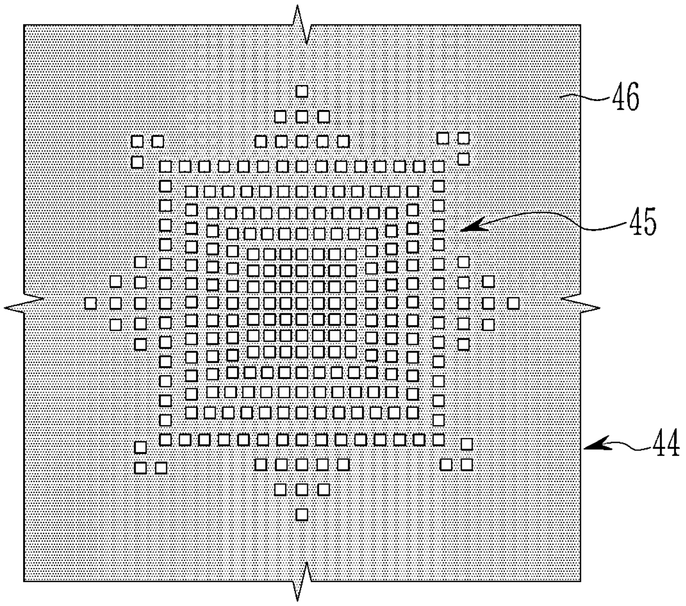

Referring to FIG. 8A to FIG. 8C, a photocurable polymer layer 42 is disposed on a transparent plate 41 such as a glass plate, and a grayscale mask 44 is disposed between a light source 43 and the transparent plate 41. The light source 43 may be composed of an ultraviolet ray collimated light exposure device, and the photo-curable polymer layer 42 may include an ultraviolet ray curable polymer.

The grayscale mask 44 is an exposure mask including a plurality of regions having different light transmission rates. In the present exemplary embodiment, the grayscale mask 44 includes a star-shaped light transmission part 45 including a plurality of protrusions extending in a radial direction, and a light blocking part 46 other than the light transmission part 45.

The light blocking part 46 may be a metal layer that blocks ultraviolet rays, and the light transmission part 45 may be an opening region from which the metal layer is removed. In FIG. 8A to FIG. 8C, an octagonal star-shaped light transmission part 45 is illustrated as an example.

In the grayscale mask 44, the light transmission part 45 has a light transmission rate that decreases further away from the center. To this end, the light transmission part 45 may be composed of a plurality of dots, and the plurality of dots may have a smaller size when moving away from the center of the light transmission part 45 (referring to FIG. 8B). On the other hand, the light transmission part 45 may be composed of a plurality of dots having the same size, and the distance between the dots may increase as the distance from the center of the light transmission part 45 increases (referring to FIG. 8C).

When the light source 43 is operated and light is irradiated to the photo-curable polymer layer 42 through the grayscale mask 44, the photo-curable polymer layer 42 at the position corresponding to the light transmission part 45 is cured by the light. At this time, the shape of the cured structure 47 corresponds to the planar shape of the light transmission part 45, and the height of the cured structure 47 is proportional to the light intensity of the light source 43 and the light transmission rate of the light transmission part 45.

As shown when the grayscale mask 44 has the octagonal star-shaped light transmission part 45 as shown in FIG. 8B and FIG. 8C, the cured structure 47 has an octagonal star-shaped pyramid shape that decreases in height as the distance from the center increases.

Figure 8D:
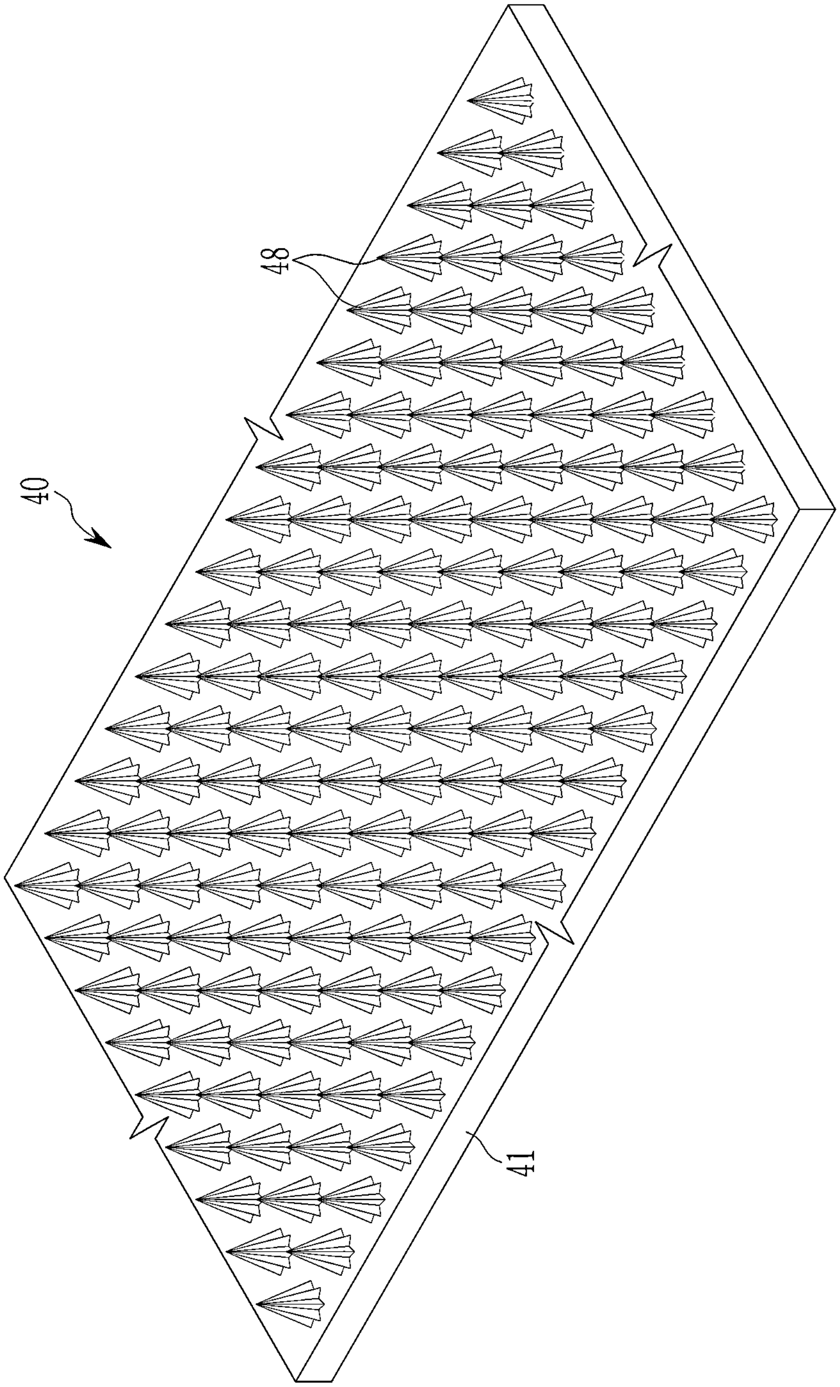

The photo-curable polymer layer 42 on the transparent plate 41 is divided into a cured part and an uncured part, and the uncured part is removed by developing. Then, as shown in FIG. 8D, the master mold 40 consisting of the transparent plate 41 and a plurality of protruded parts 48 arranged on one surface of the transparent plate 41 is completed. A plurality of protruded part 48 consists of an octagonal star-shaped pyramid.

Figure 9:
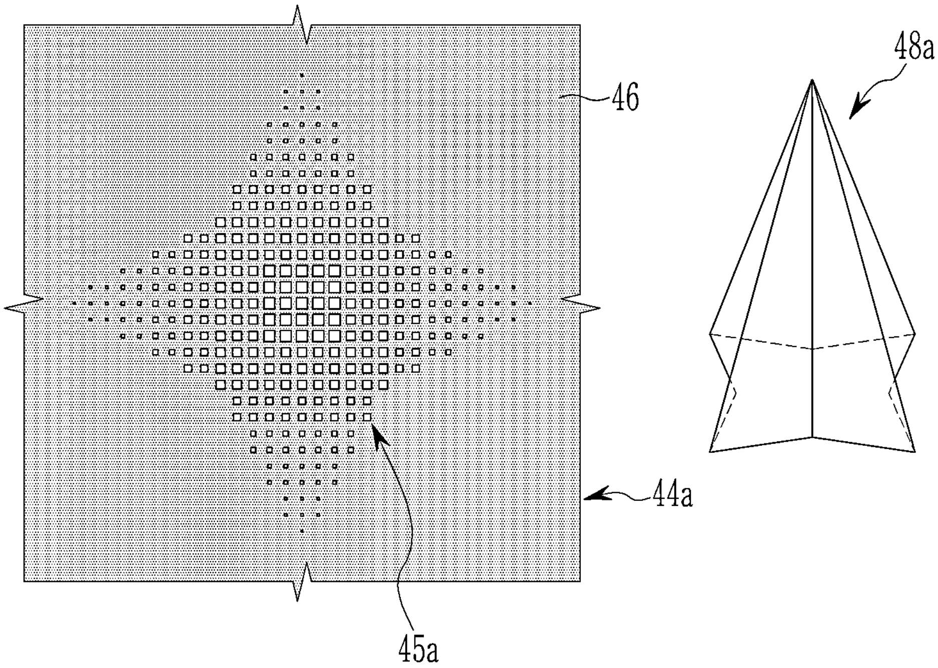
FIG. 9 to FIG. 11 are views showing a light transmission part shown in FIG. 8A and a protruded part shown in FIG. 8D according to an exemplary variation.
Figure 10:
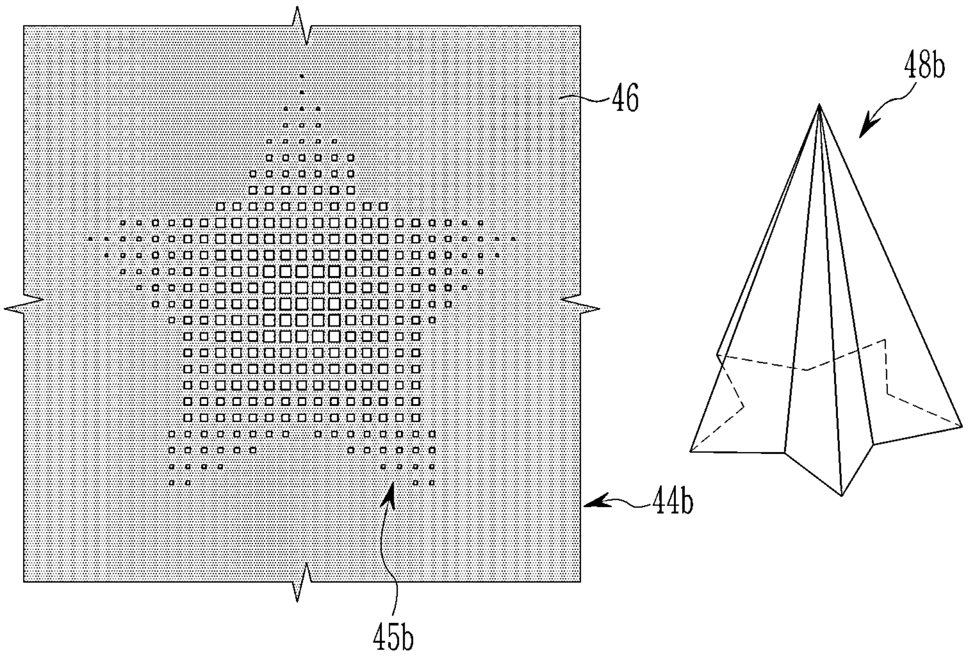
Figure 11:
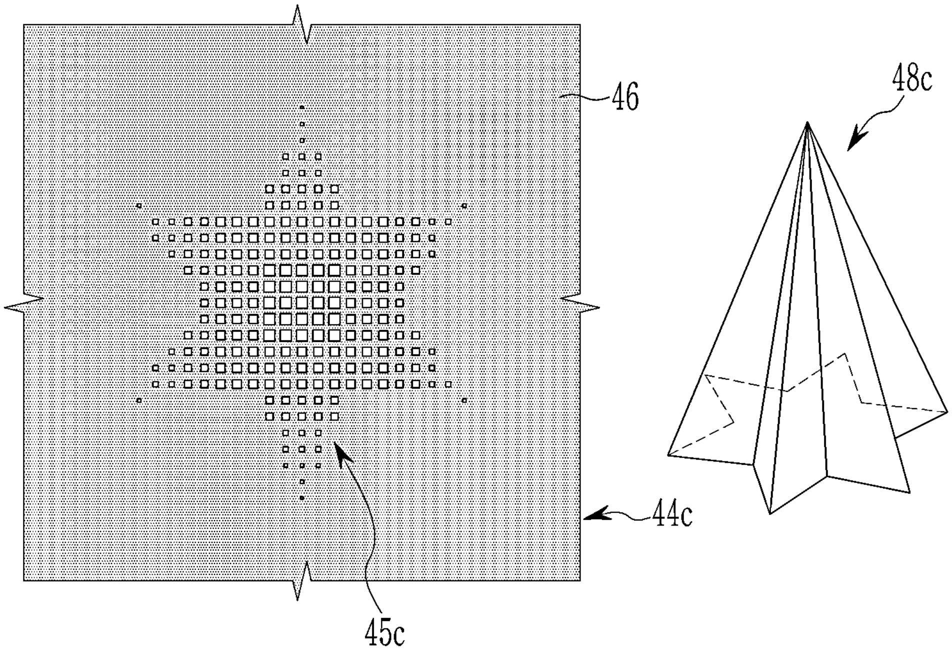

FIG. 9 to FIG. 11 are views showing a light transmission part shown in FIG. 8A and a protruded part shown in FIG. 8D according to an exemplary variation.

Referring to FIG. 9, the light transmission part 45*a* includes four protrusions extending in a radial direction and has a light transmission rate that decreases away from the center. The protruded part 48*a* of the master mold manufactured by using this grayscale mask 44*a* is made as a square star-shaped pyramid.

Referring to FIG. 10, the light transmission part 45*b* includes five protrusions extending in a radial direction and has a light transmission rate that decreases as the distance from the center increases. The protruded part 48*b* of the master mold manufactured by using this grayscale mask 44*b* is made as a pentagonal star-shaped pyramid.

Referring to FIG. 11, the light transmission part 45*c* includes six protrusions extending in a radial direction and has a light transmission rate that decreases as the distance from the center increases. The protruded part 48*c* of the master mold manufactured by using this grayscale mask 44*c* is made as a hexagonal star-shaped pyramid.

FIG. 9 to FIG. 11 illustrates the light transmission parts 45*a*, 45*b*, and 45*c*, which are composed as a plurality of dots having a smaller size as the distance from the center increases as an example, but the light transmission parts 45*a*, 45*b*, and 45*c* may be composed of a plurality of dots between which the distance increases further away from the center while all have the same size as shown in FIG. 8C.

By changing the shape of the light transmission part 45 in this way, it is possible to manufacture the star-shaped pyramid protruded part 48 having a number of protrusions included in the range of 3 or more, preferably 3 to 20.

Figure 12A:
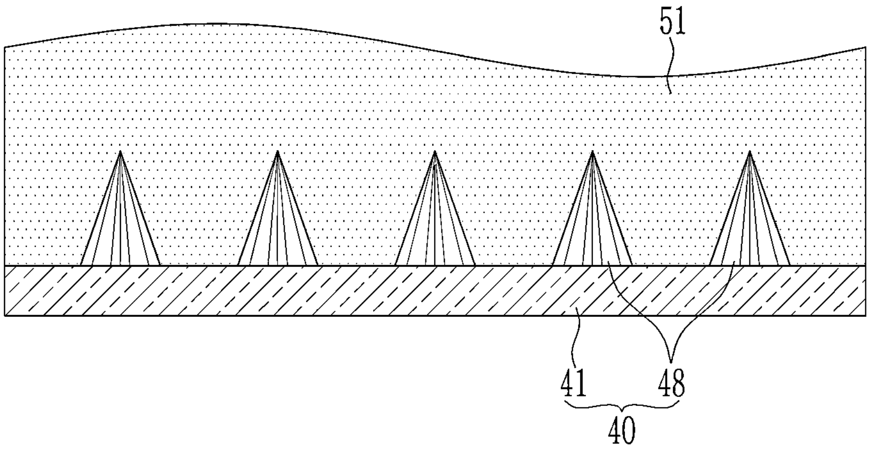
FIG. 12A to FIG. 12C are views showing a mold manufacturing process of a second step shown in FIG. 7.
Figure 12B:
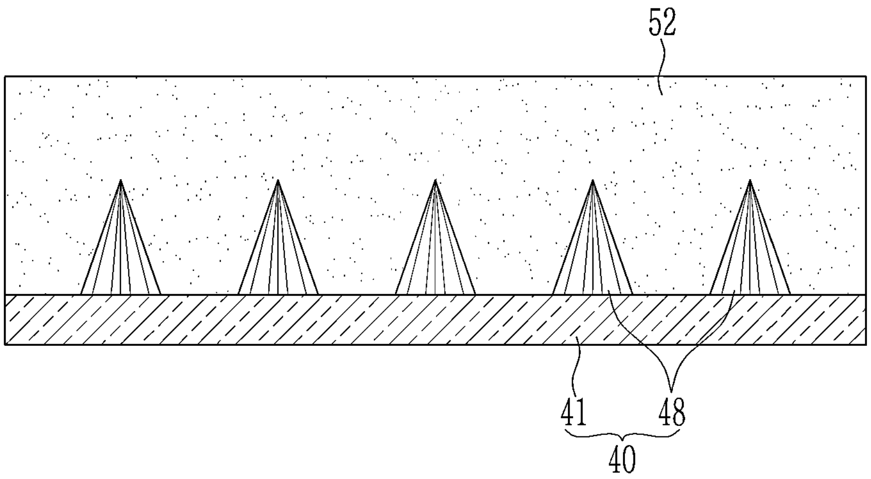
Figure 12C:
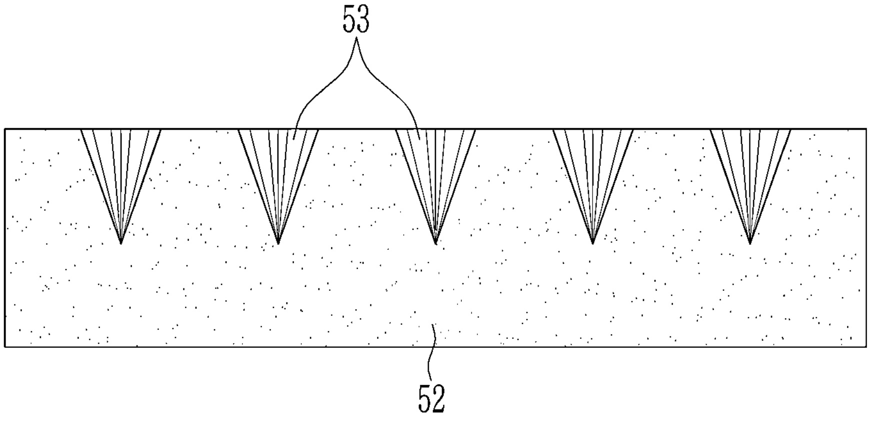

FIG. 12A to FIG. 12C are views showing a mold manufacturing process of a second step shown in FIG. 7.

Referring to FIG. 12A to FIG. 12C, a polymer solution is coated on the master mold 40 to form a polymer layer 51. The polymer layer 51 may include a thermosetting resin. The polymer layer 51 may include, for example, polydimethylsiloxane, but is not limited to this example.

At this time, since fine bubbles may be disposed around the surface of the polymer layer 51 in contact with the master mold 40, a method of applying a negative pressure to the polymer layer 51 by using a vacuum device (although not shown) may be used to remove the fine bubbles.

Subsequently, heat is applied to the polymer layer 51 to be cured, and the master mold 40 is separated from the cured mold 52 to complete the mold 52 having a plurality of recess portions 53. The mold 52 may have a plate structure with a predetermined thickness, and a plurality of recess portions 53 having the shape corresponding to the protruded part 48 of the master mold 40 are disposed on one surface of the mold 52.

Figure 14A:
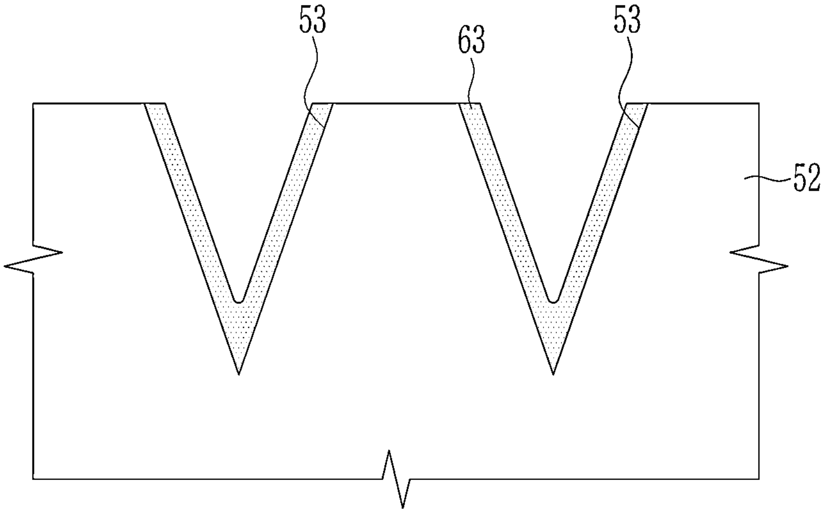
FIG. 14A to FIG. 14C are views showing a patch manufacturing process shown in FIG. 13A to FIG. 13D according to an exemplary variation.
Figure 14B:
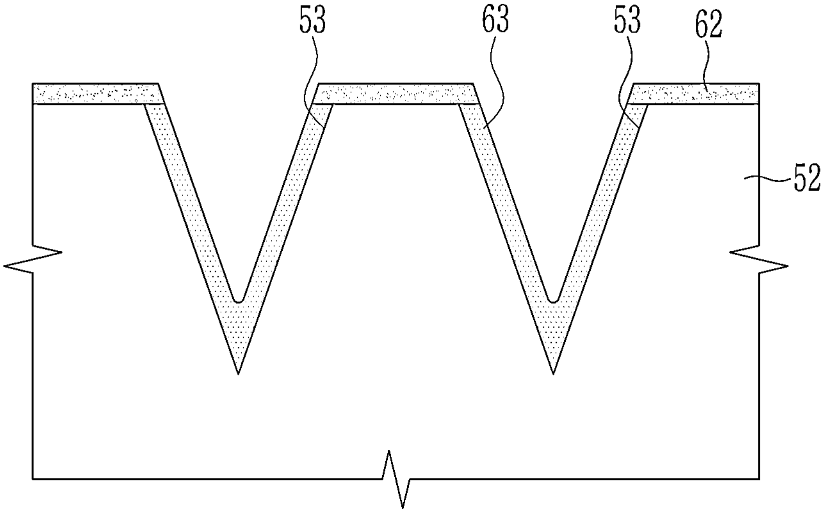
Figure 14C:
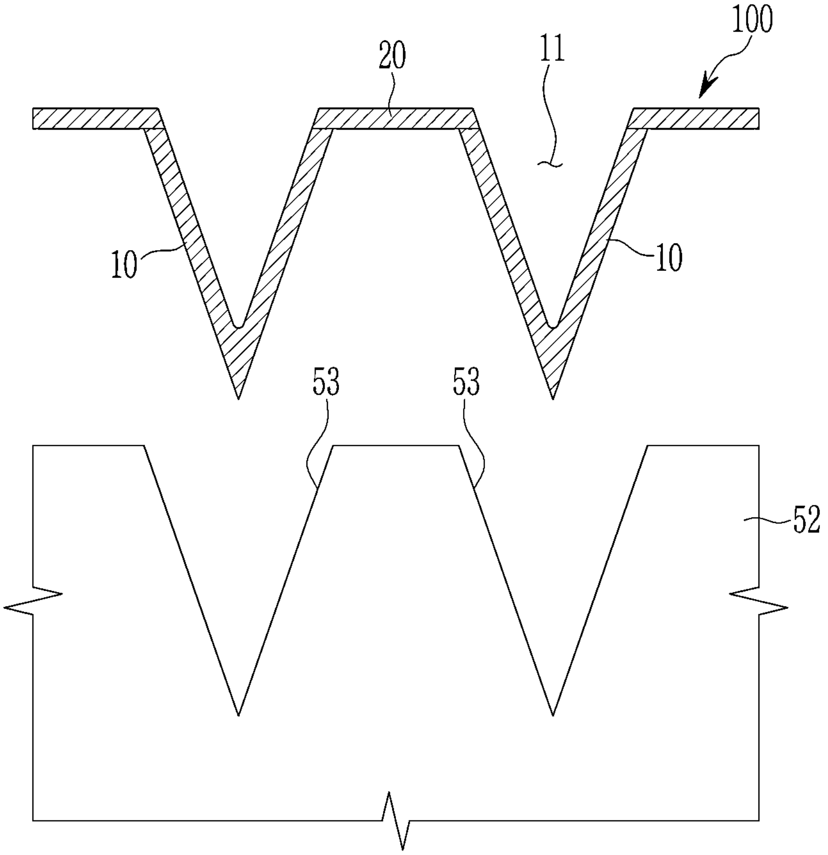
Figure 15A:
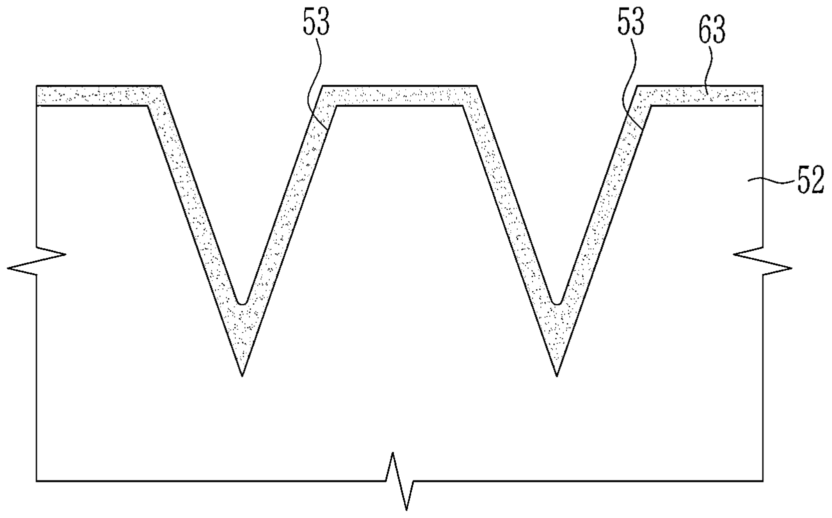
FIG. 15A and FIG. 15B are views showing a patch manufacturing process shown in FIG. 13A to FIG. 13D according to another exemplary variation.

The patch manufacturing process of the third step shown in FIG. 7 may be accomplished by any of following three methods. FIG. 13A to FIG. 13D show the first method, FIG. 14A to FIG. 14C show the second method, and FIG. 15A and FIG. 15C show the third method.

FIG. 13A to FIG. 13D are views showing a patch manufacturing process of a third step shown in FIG. 7.

Figure 13A:
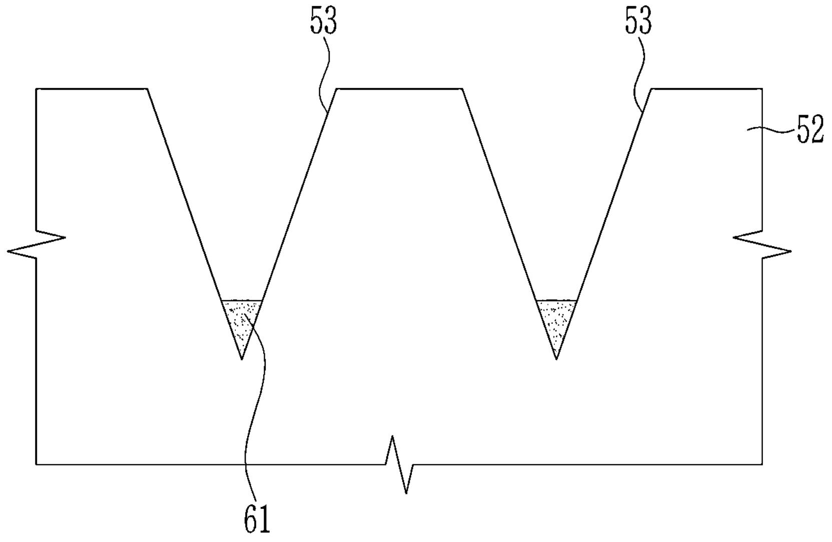
FIG. 13A to FIG. 13D are views showing a patch manufacturing process of a third step shown in FIG. 7.
Figure 13B:
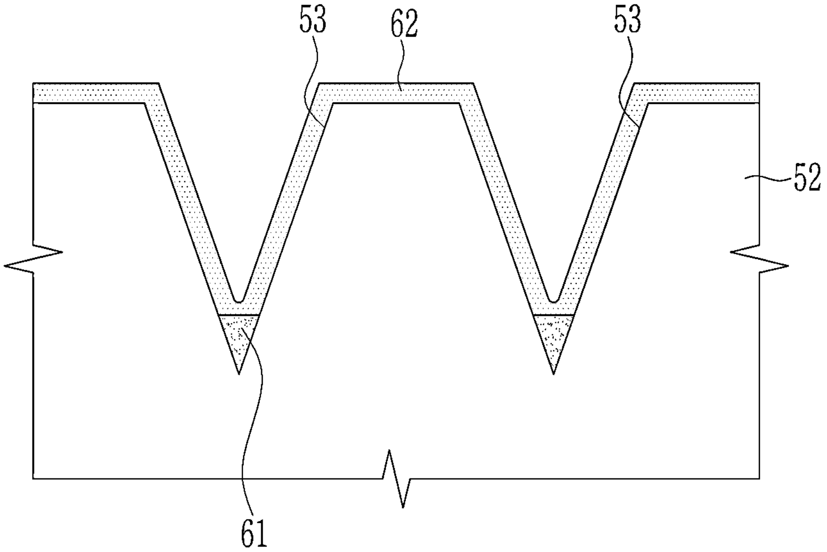

Referring to FIG. 13A and FIG. 13B, the drug 61 is injected to each pointed end portion of a plurality of recess portions 53 and a biodegradable polymer solution 62 is thinly coated on the surface of the mold 52 between each wall surface of a plurality of recess portions 53 so that the biodegradable polymer solution 62 continues seamlessly along the curvature of the mold 52 surface.

That is, the biodegradable polymer solution 62 is disposed at a predetermined thickness along each wall of a plurality of recess portions 53 and is also disposed at a predetermined thickness on the surface of the mold 52 between a plurality of recess portions 53. The thickness of the biodegradable polymer solution 62 coated to the mold 52 may be less than half of the depth of the recess portion 53, and microbubbles may exist on the surface or inside the drug 61 and the biodegradable polymer solution 62.

Figure 13C:
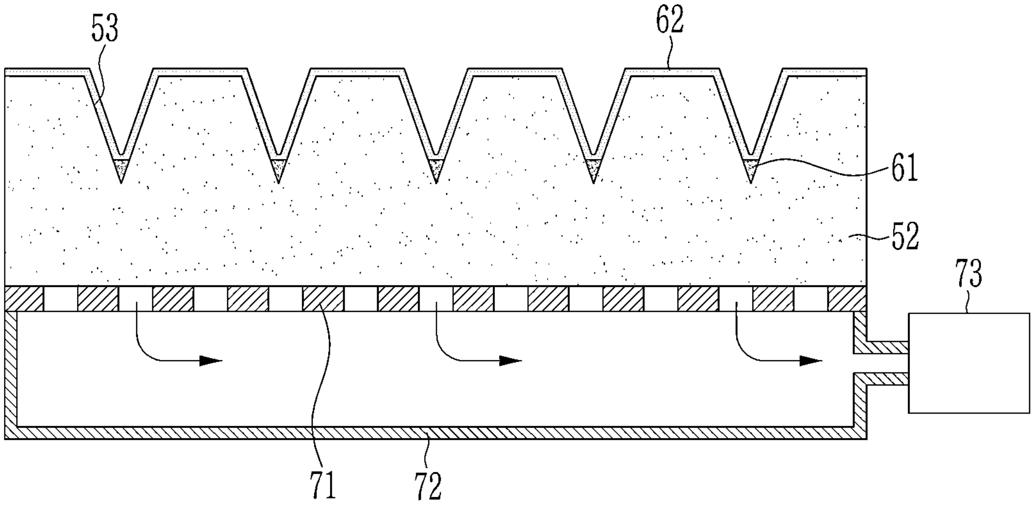

Referring to FIG. 13C, a vacuum filter 71 and a vacuum chamber 72 are disposed on the rear of the mold 52. The vacuum filter 71 is composed of a porous plate in which a plurality of holes are formed, and the vacuum chamber 72 includes an internal space connected to a vacuum pump 73. The mold 52 has an ultra-fine porous structure that is hardened but has numerous micropores inside.

When the vacuum pump 73 is operated, a negative pressure is applied to the drug 61 and the biodegradable polymer solution 62 through the vacuum filter 71 and the mold 52. The negative pressure at this time is not a pressure applied in all directions and is a pressure in a single direction from the drug 61 and the biodegradable polymer solution 62 toward the mold 52.

By using the negative pressure in a single direction applied from the back side of the mold 52, microbubbles contained within the drug 61 and biodegradable polymer solution 62 may be easily removed without deforming them.

Figure 13D:
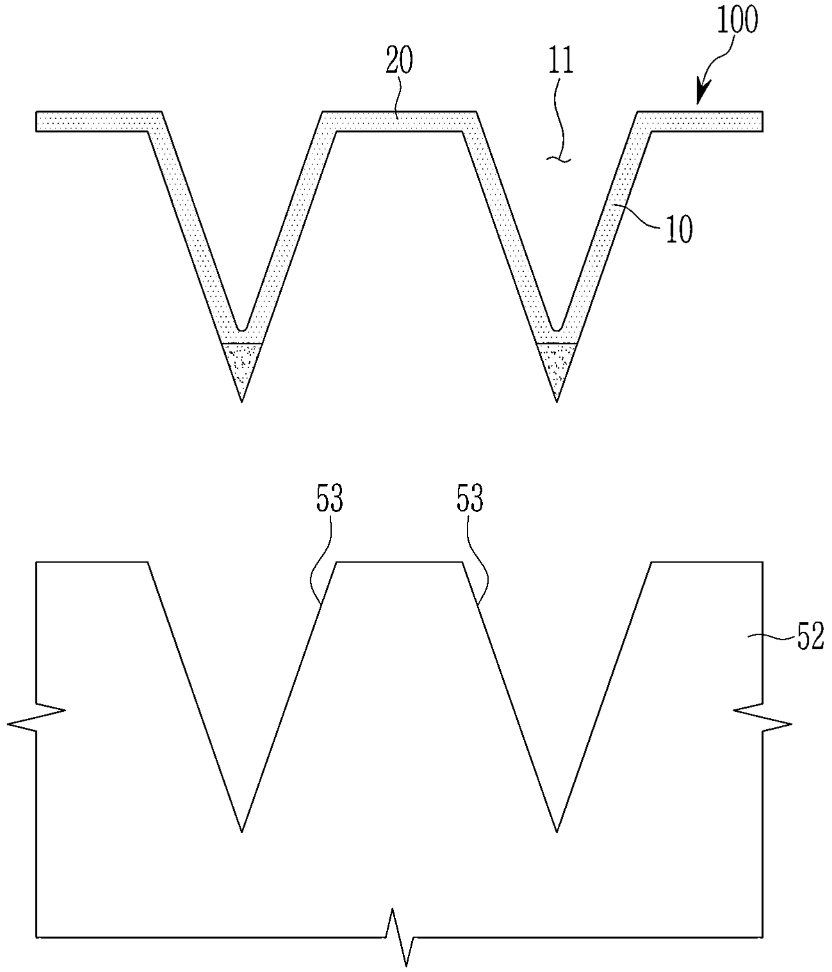

Referring to FIG. 13D, the drug 61 and the biodegradable polymer solution 62 are dried and hardened into a patch 100 of a solid type, and then the patch 100 is separated from the mold 52. The patch 100 is composed of a plurality of microneedles 10 in which the drug is concentrated in a pointed end portion while having an empty space 11 therein and a base layer 20 connecting a plurality of microneedles 10.

FIG. 14A to FIG. 14C are views showing a patch manufacturing process shown in FIG. 13A to FIG. 13D according to an exemplary variation.

Referring to FIG. 14A to FIG. 14C, the drug of a powder or liquid form is dispersed into a biodegradable polymer solution to prepare a material solution 63, and the material solution 63 is coated thinly along each wall of a plurality of recess portions 53. The thickness of the coated material solution 63 may be less than half the depth of the recess portion 53.

Then, the biodegradable polymer solution 62 is coated to the surface of the mold 52 between a plurality of recess portions 53. The negative pressure in the single direction is then applied from the back side of the mold 52, to the material solution 63 and the biodegradable polymer solution 62 to remove the microbubbles contained in the material solution 63 and biodegradable polymer solution 62 (referring to FIG. 13C).

Subsequently, the material solution 63 disposed in a plurality of recess portions 53 and the biodegradable polymer solution 62 on the surface of the mold 52 are dried and hardened into the patch 100 of a solid type, and then the patch 100 is separated from the mold 52.

The patch 100 is composed of a plurality of microneedles 10 in which the drug is uniformly dispersed while having an empty space 11 therein and a base layer 20 connecting a plurality of microneedles 10.

Figure 15B:
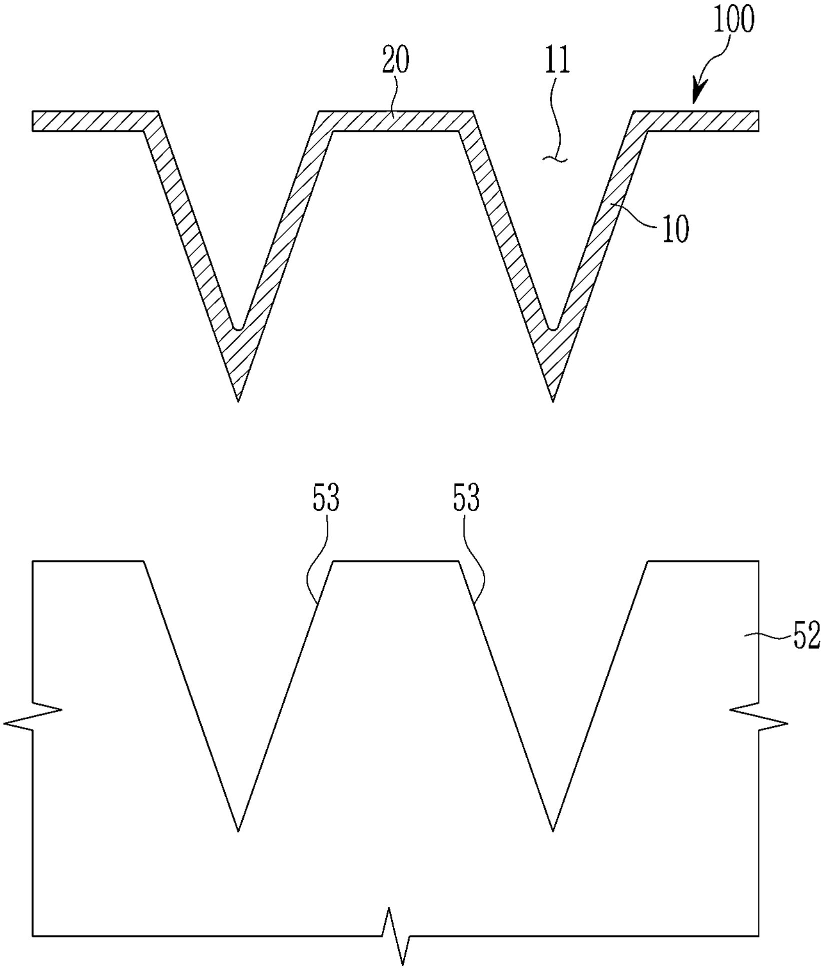

FIG. 15A and FIG. 15B are views showing a patch manufacturing process shown in FIG. 13A to FIG. 13D according to another exemplary variation.

Referring to FIG. 15A and FIG. 15B, the drug of a powder or liquid form is dispersed into a biodegradable polymer solution to prepare the material solution 63, and the material solution 63 is thinly coated on the surface of the mold 52 between each wall surface of a plurality of recess portions 53 53 so that the material solution 63 continues seamlessly along the curvature of the mold surface. The thickness of the coated material solution 63 may be less than half the depth of the recess portion 53.

And, the microbubbles contained in the material solution 63 are removed by applying the negative pressure in the single direction to the material solution 63 from the back side of the mold 52 (referring to FIG. 13C). Then, the material solution 63 is dried and hardened into the patch 100 of a solid type, and then the patch 100 is separated from the mold 52.

The patch 100 is composed of a plurality of microneedles 10 having an empty space 11 therein and a base layer 20 connecting a plurality of microneedles 10, and the plurality of microneedles 10 and the base layer 20 include the drug that is uniformly dispersed.

According to the above-described method, a plurality of molds 52 can be mass-produced by manufacturing one master mold 40, and the patch 100 may be easily manufactured by using a plurality of molds 52. In addition, it is possible to manufacture a plurality of microneedles 10 having excellent shape precision without air bubbles on the surface or inside.

A plurality of microneedles 10 included in the patch 100 are formed of the same star-shaped pyramid as the protruded part 48 of the master mold 40 while having the empty space 11 inside.

While this invention has been described in connection with what is presently considered to be practical exemplary embodiments, it is to be understood that the invention is not limited to the disclosed embodiments. On the contrary, it is intended to cover various modifications and equivalent arrangements included within the scope of the appended claims.

The invention claimed is:

1. A transdermal drug delivery patch comprising:

a flexible base layer; and a plurality of microneedles disposed at one surface of the base layer, including a biodegradable polymer and a drug, and having an empty space inside, wherein each of the plurality of microneedles is formed of a star-shaped pyramid including a plurality of protrusions extending in a radial direction, a part between two protrusions adjacent along the circumferential direction among the plurality of protrusions is concave, and wherein a plurality of openings are disposed in the base layer, and the plurality of openings respectively communicate with empty spaces of the plurality of microneedles, wherein the two protrusions adjacent along the circumferential direction among the plurality of protrusions are connected at an angle, wherein the empty space of each of the plurality of microneedles has a shape corresponding to the star-shaped pyramid.

2. The transdermal drug delivery patch of claim 1, wherein an opening of each empty space of the plurality of microneedles is one of the plurality of openings in the base layer.

3. The transdermal drug delivery patch of claim 1, wherein in each of a plurality of microneedles, all protruded lengths of each of the plurality of protrusions according to the radial direction are the same, and all distances between two protrusions adjacent along the circumferential direction among the plurality of protrusions are the same.

4. The transdermal drug delivery patch of claim 3, wherein a number of the plurality of protrusions is 3 or more and 20 or less.

5. The transdermal drug delivery patch of claim 1, wherein in each of the plurality of microneedles, the drug is concentrated at a pointed end portion of the microneedle.

6. The transdermal drug delivery patch of claim 1, wherein in each of the plurality of microneedles, the drug is uniformly distributed on the entire microneedle.

* * * * *